US010288530B2

(12) United States Patent
Sundermeyer et al.

(10) Patent No.: US 10,288,530 B2
(45) Date of Patent: May 14, 2019

(54) METHOD FOR IMPROVING SEVERITY ESTIMATES

(71) Applicant: Caterpillar Inc., Peoria, IL (US)

(72) Inventors: Jeffry N. Sundermeyer, Dunlap, IL (US); Benjamin Hodel, Dunlap, IL (US); Nathan J. Wieland, Eureka, IL (US); Jim A. Nygaard, Washington, IL (US)

(73) Assignee: Caterpillar Inc., Deerfield, IL (US)

( * ) Notice: Subject to any disclaimer, the term of this patent is extended or adjusted under 35 U.S.C. 154(b) by 871 days.

(21) Appl. No.: 14/727,022

(22) Filed: Jun. 1, 2015

(65) Prior Publication Data

US 2016/0349151 A1 Dec. 1, 2016

(51) Int. Cl.
G01M 5/00 (2006.01)
G01M 99/00 (2011.01)
G05B 23/02 (2006.01)
G06Q 10/00 (2012.01)

(52) U.S. Cl.
CPC ........ G01M 99/005 (2013.01); G01M 5/0033 (2013.01); G05B 23/024 (2013.01); G05B 23/0283 (2013.01); G06Q 10/20 (2013.01); G01N 2203/0073 (2013.01)

(58) Field of Classification Search
CPC ........................ G01M 99/005; G01M 99/008
See application file for complete search history.

(56) References Cited

U.S. PATENT DOCUMENTS

| 6,448,488 | B1 * | 9/2002 | Ekhaus ................. G10H 1/125 84/622 |
| 7,260,501 | B2 | 8/2007 | Pattipatti et al. |
| 7,505,844 | B2 | 3/2009 | Wiseman et al. |
| 8,086,640 | B2 | 12/2011 | Grichnik et al. |
| 8,667,332 | B2 | 3/2014 | Bharadwaj et al. |
| 9,964,468 | B1 * | 5/2018 | Wu ........................ G01M 99/00 |
| 2010/0100338 | A1 * | 4/2010 | Vik ..................... G01M 5/0033 702/42 |
| 2014/0047271 | A1 | 2/2014 | Gray et al. |
| 2014/0058709 | A1 * | 2/2014 | Machado Viana .. G01M 5/0033 703/2 |

OTHER PUBLICATIONS

Rensfelt, Optimal sensor locations for nonparametric identification of viscoelastic materials, Automatica 44 (2008) 28-38.*

(Continued)

Primary Examiner — Michael J Dalbo
(74) Attorney, Agent, or Firm — Lee & Hayes, PLLC

(57) ABSTRACT

A method for providing improved composite work cycle damage estimates includes constructing a damage rate basis matrix, performing a D-optimal row selection calculation on the damage rate basis matrix, selecting, based on the D-optimal row selection calculation, a finite number of strain measurement device locations on the machine, extracting a target percentile damage rate for each of the one or more strain measurement devices, and using the extracted damage rates to solve for the unknown coefficients and verify the weightings assigned to the machine operations.

20 Claims, 3 Drawing Sheets

(56) References Cited

OTHER PUBLICATIONS

Gupta, Inverse Methods for Load Identification Augmented by Optimal Sensor Placement and Model Order Reduction, (2013), Theses and Dissertations, Paper 357.*
A.M. Madni, L.A. Wan, "Microelectromechanical systems (MEMS): an overview of current state-of-the-art", Aerospace Conference 1998 IEEE, vol. 1, pp. 421-427 vol. 1, 1998, ISSN 1095-323X.*
Kessler, A Structural Health Monitoring Software Tool for Optimization, Diagnostics and Prognostics, Annual Conference of the Prognostics and Health Management Society, 2011.*
Kincaid et al., D-optimal designs for sensor and actuator locations, Computers & Operations Research 29 (2002), Elsevier Science Ltd. 701-713.*

* cited by examiner

METHOD FOR IMPROVING SEVERITY ESTIMATES

TECHNICAL FIELD

The present disclosure relates to composite work cycles and more particularly to a method for improving severity testing in composite work cycles.

BACKGROUND

Composite work cycles (CWC) are important aspects of product development and validation processes for many equipment manufacturers. CWCs may be defined as a carefully selected set of defined test events intended to map to a desired percentile in a severity response distribution. Unfortunately, the variability in equipment application and severity in the user base may be high and poorly understood. Accordingly, a defined composite work cycle may not closely map to desired severity percentiles. For example, a composite work cycle may suffer from unnecessary redundancy in event definition, or may be lacking a specified event to be input in order to accurately map to the desired percentile of severity.

U.S. Pat. No. 8,571,814 to Zhao discloses a structural load monitoring system incorporating a load monitoring reliability factor. According to one embodiment, Zhao provides a method including accessing distributions of flight loads associated with one or more flight regimes for a fleet of aircraft. Using the distributions of flight loads, a factor for a flight regime is determined that provides a flight load adjustment for a component on each aircraft of a fleet of aircraft known to be affected through load damage by the flight regime. Such structural health predictions are used to determine when to replace various aircraft components. However, Zhao does not relate to using a D-optimal selection process to provide improved severity estimates.

Accordingly, it is advantageous to provide improved severity testing using a D-optimal selection process.

SUMMARY OF THE INVENTION

According to an aspect of the disclosure, a method for providing improved composite work cycle damage estimates includes constructing a damage rate basis matrix, the damage rate basis matrix configured to be multiplied by a plurality of unknown coefficients representing weightings assigned to machine operations, performing a D-optimal row selection calculation on the damage rate basis matrix, selecting, based on the D-optimal row selection calculation, a finite number of strain measurement device locations on the machine, wherein the finite number of strain measurement device locations optimizes use of one or more strain measurement devices to be placed on the machine, extracting a target percentile damage rate for each of the one or more strain measurement devices, and using the extracted damage rates to solve for the unknown coefficients and verify the weightings assigned to the machine operations.

According to one aspect of the disclosure, a computer-readable medium is provided. A processor may be configured to execute instructions stored on a computer-readable medium to perform a method including constructing a damage rate basis matrix, the damage rate basis matrix configured to be multiplied by a plurality of unknown coefficients representing weightings assigned to machine operations, performing a D-optimal row selection calculation on the mathematical mapping, selecting, based on the D-optimal row selection calculation, a finite number of strain measurement device locations on the machine, wherein the finite number of strain measurement device locations optimizes use of one or more strain measurement devices to be placed on the machine, extracting a target percentile damage rate for each of the one or more strain measurement devices, and using the extracted damage rates to solve for the unknown coefficients and verify the weightings assigned to the machine operations.

Other features and aspects of this disclosure will be apparent from the following description and the accompanying drawings.

BRIEF DESCRIPTION OF THE DRAWINGS

The accompanying drawings, which are incorporated in and constitute a part of this specification, illustrate several aspects of the disclosure and together with the description, serve to explain the principles of the disclosure. In the drawings.

DETAILED DESCRIPTION

Reference will now be made in detail to aspects of the disclosure, examples of which are illustrated in the accompanying drawings. Wherever possible, the same reference numbers will be used throughout the drawings to refer to the same or like parts or elements.

Figure 1:
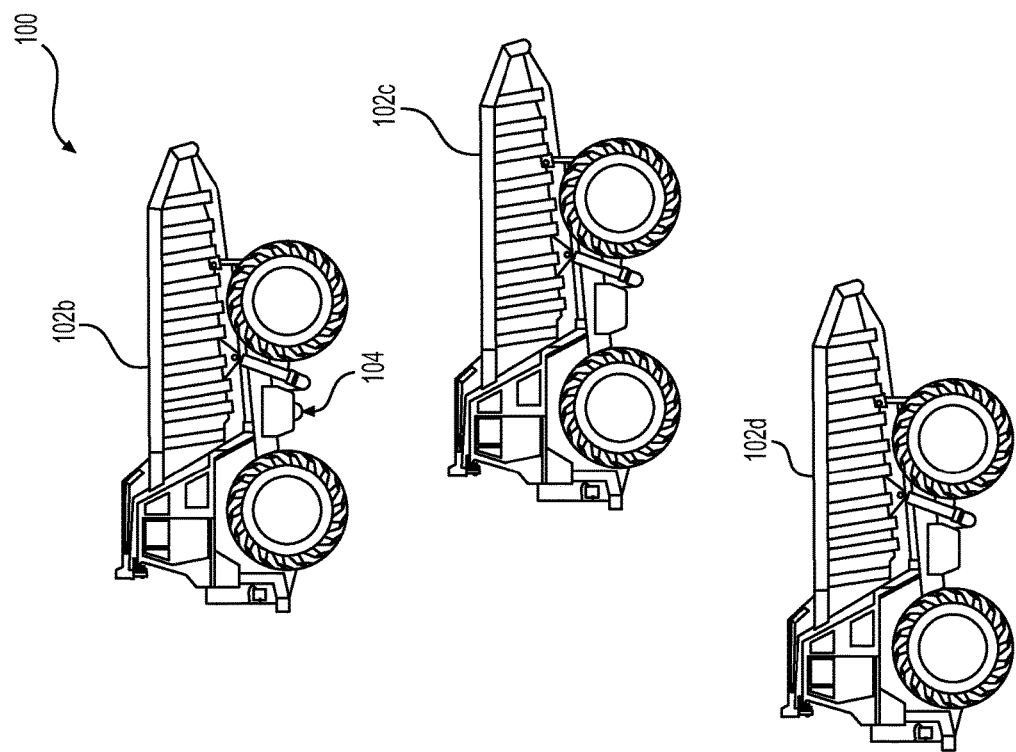
FIG. 1 illustrates a machine environment according to embodiments of the present disclosure.
Figure 1:
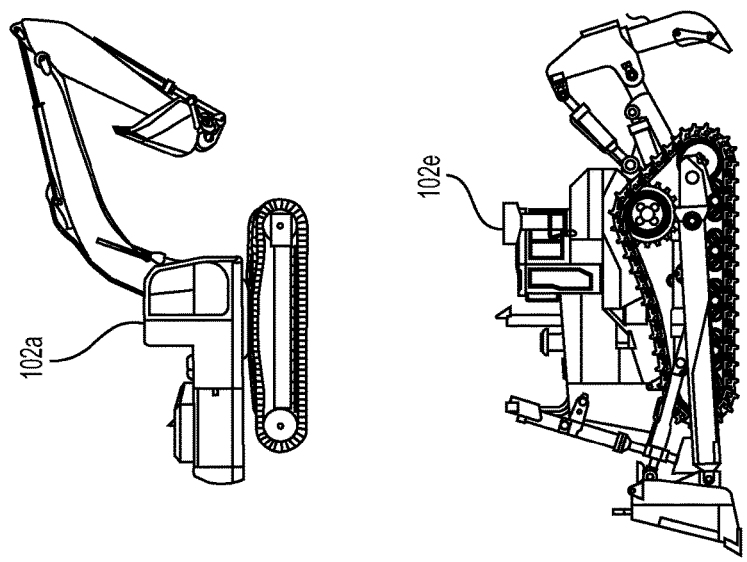

FIG. 1 illustrates a typical worksite 100 where a plurality of machines and or equipment may be deployed to perform a set of work tasks (e.g., a mine site, a construction site, etc.). As shown in FIG. 1, worksite 100 may include one or more machines 102a-102e, hereinafter also collectively referred as machine 102 or machines 102. A machine, as the term is used herein, refers to a fixed or mobile machine that performs some type of operation associated with a particular industry, such as mining, construction, farming, etc. and operates between or within work environments (e.g., construction site, mine site, power plant, etc.). A non-limiting example of a fixed machine includes an engine system operating in an off-shore plant environment (e.g., off-shore drilling platform). Non-limiting examples of mobile machines include commercial machines, such as trucks (e.g., mining trucks, haul trucks, on-highway trucks, off-highway trucks, articulated trucks, etc.), cranes, draglines, pipe layers, earth moving vehicles, mining vehicles, backhoes, loaders (e.g., large wheel loaders, track-type loaders, etc.), shovels, material handling equipment, farming equipment, marine vessels, aircraft, and any type of movable machine that operates in a work environment. Such machines deployed on a worksite (e.g., worksite 100) may be manned machines, autonomous machines or semi-autonomous machines. The machines 102 may also include one or more strain measurement devices 104 (e.g., wireless or wired fatigue nodes, strain gauges, rosettes, or other such devices used to measure strain on machines or machine components) from which strain data may be received by one or more of the above modules (e.g., electronic control module 112).

Figure 2:
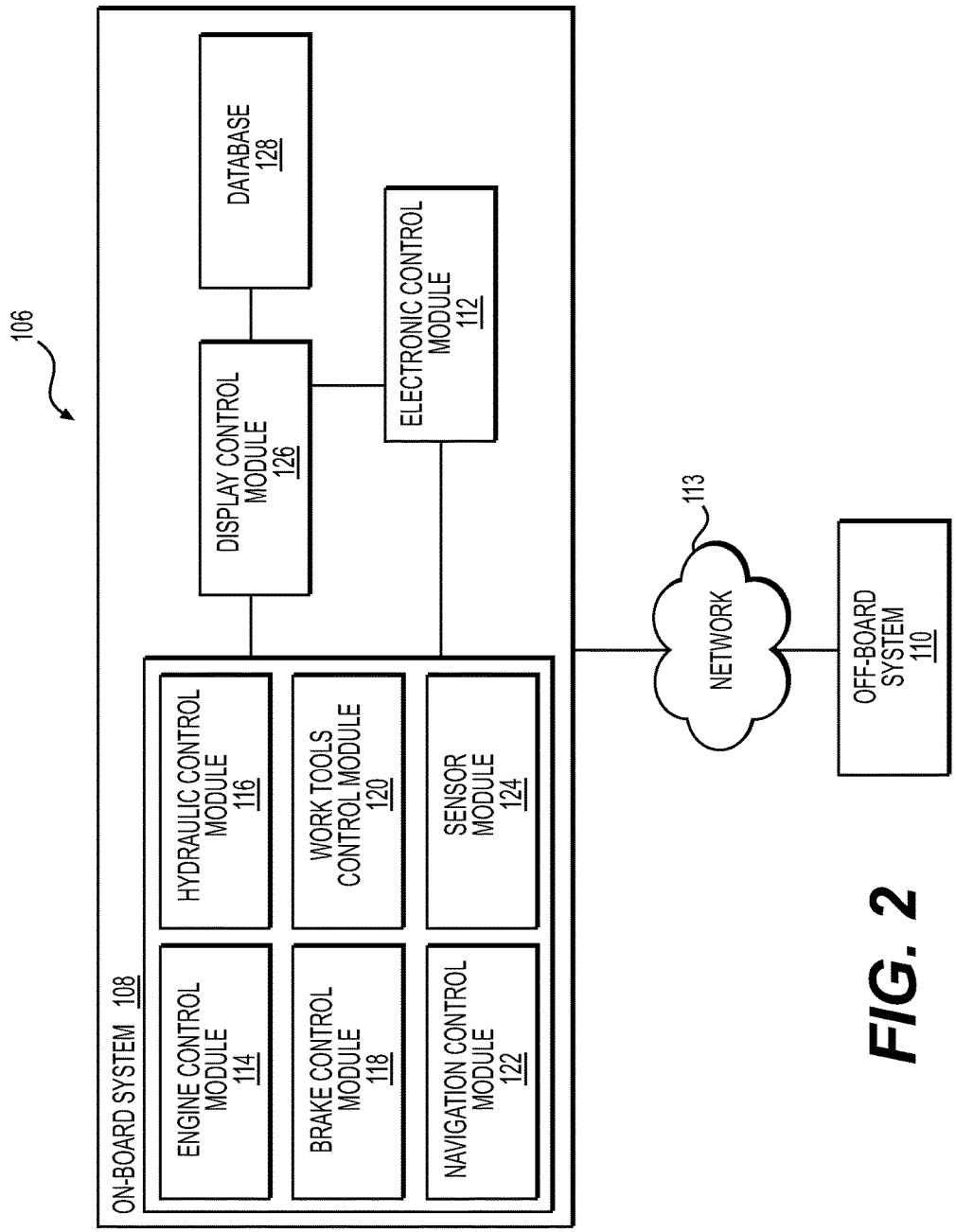
FIG. 2 illustrates a block diagram of a system that may be configured to perform functions according to embodiments of the present disclosure.

A machine 102 may include on-board communications, monitoring systems, and controls. FIG. 2 illustrates a block diagram of a system 106 that may be configured to perform functions within the environment 100 described in FIG. 1. In some embodiments, system 106 includes an on-board system 108 and an off-board system 110. On-board system 108 may include an operator display device and may include any type of power system control module or attachment interface that connects one or more sub-components. Machine 102 may use the on-board system 108 to facilitate operations of the machine during run time or non-run time conditions (i.e., machine engine running or not running, respectively). For instance, on-board system 108 may include various modules for capturing and analyzing machine data (e.g., electronic control module 112, engine control module 114, hydraulic control module 116, brake control module 118, work tools control module 120, Global Positioning System (GPS)/navigation control module 122, sensor module 124, display module 126, etc). Referring back to FIG. 1, the machines 102 may also include one or more strain measurement devices 104 from which strain data may be received by one or more of the above modules (e.g., electronic control module 112).

It is to be appreciated that on-board system 108, as the term is used herein, may represent any type of component operating in machine 102 that controls or is controlled by other components or sub-components. In one embodiment, the on-board system 108 may be embodied as a remote control station capable of receiving data from one or more control modules (e.g., the engine control module 114) on-board each of the machines 102. In another embodiment, on-board system 108 may be configured to control an operation of the machine 102 based on the monitoring of data (e.g., sensor data, accelerometer data, hydraulic pressure data). One or more modules of on-board system 108 may communicate with other on-board modules to perform various functions related to the operation of the machine 102. For example, display module 126 may receive data from an engine control module 114 via a data link (e.g., a J1939 data link), while engine control module 114 supplies estimated torque and fuel information to hydraulic control module 116 via proprietary data links. In some embodiments, non-control modules may process the data on-board, or data may be processed near-on-board or off-board.

Once strain data is collected, it may then be transferred off-board. Thus, machine 102 or any control component thereof may also be connected to an off-board system 110 (e.g., centralized server, a remote data management system, off-board computing system, etc.) associated therewith. An off-board system, as the term is used herein, may represent a system that is located remote from a machine, such as remote from machine 102. Off-board system 110 may be a workstation, personal digital assistant, laptop, mainframe, etc., and may include one or more computing systems each executing one or more software applications. The off-board system 110 may be implemented in a worksite or in a vicinity proximate to one or more worksites (e.g., worksite 100).

Off-board system 110 may include various hardware devices and modules for monitoring, capturing, and/or analyzing machine data related to the machines operating on the given worksite. For instance, to perform various monitoring and/or control functions, off-board system 110 may include known computing components, such as one or more processors, analysis modules and software, display, and interface devices that operate collectively to perform one or more processes. In certain embodiments, off-board system 110 may include one or more controllers, such as Programmable Logic Controllers (PLCs) that may be used in plants and/or factories. Alternatively, or additionally, the off-board system 110 may include one or more communications devices that facilitate the transmission of data to and from an on-board system (e.g., on-board system 108). Off-board system 110 may also be associated with a user (e.g., customer), multiple users, a business entity (dealer, manufacturer, vendor, etc.), a department of a business entity (e.g., service center, operations support center, logistics center, etc.), and any other type of entity that sends and/or receives information to/from on-board system 108. Further, off-board system 110 may execute off-board software applications that download or upload information to/from on-board system 108 via a network 113.

Figure 3:
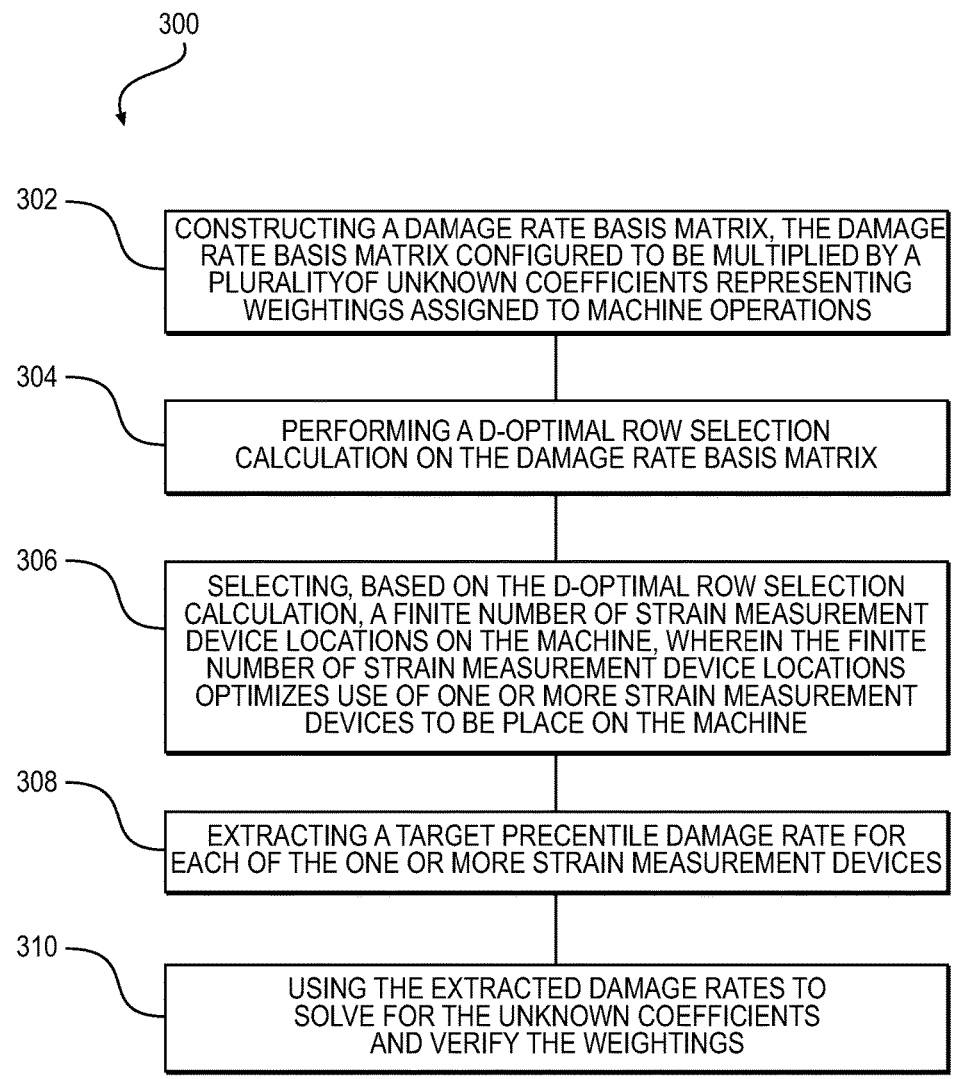
FIG. 3 illustrates a flowchart of an exemplary process providing improved severity estimates using D-optimal selection according to embodiments of the present disclosure.

FIG. 3 is a flowchart of a method 300 for using D-optimal location selection to improve composite work cycles. It is contemplated that method 300 may be performed in any order suitable for verifying simulated severity test measurements align with actual severity responses, according to embodiments of the disclosure. Method 300 is described for illustration purposes only with respect to the worksite environment and machine components and processes depicted in FIGS. 1-2. However, it should be apparent that method 300 may be employed with other systems and interfaces. Further, the order of operations of FIG. 3 should not be considered limiting.

Method 300 may begin at operation 302, where a damage rate basis matrix is constructed. The damage rate basis matrix includes a plurality of unknown coefficients representing weightings assigned to machine operations. In some embodiments, the damage rate basis matrix equation that relates test severity to a targeted percentile of user-observed severity may be seen in the equation below:

$$\{\overline{D}_{obs}\} = [\overline{d}_{bas}]\{p\}$$

where the left hand side column vector is a set of 90th percentile (or any other targeted percentile) observed severity responses, commonly expressed as fatigue damage rates. The damage rate basis matrix on the right hand side is a matrix where each row corresponds to a location on the structural system of interest, and each column corresponds to a test event in the composite work cycle. The column vector "$\{p\}$" on the right hand side is a column vector of unknown quantities that map a test facility's test basis matrix into the user-observed 90th percentile damage rate column vector and is configured to multiply the matrix. One or more virtual or measured load histories for each event in a composite work cycle may be sent through finite element models so that strain and fatigue may be calculated for all locations on a particular machine. Measured load data may be received from a set of machines selected to be monitored for severity. In a preferred embodiment, the set of machines includes one type of machine (e.g., a wheel loader, a track-type tractor, etc.) such as machine 104 described above. For instance, a set of machines may be selected to have a plurality of strain measurement devices (e.g., strain measurement device 104) installed on them. The strain measurement devices 104 may also be programmed with an arbitrary S-N curve, and may be configured to sample strains at up to 512 Hz. The strain measurement devices 104 may calculate accumulated damage at user-specified planes in the strain measurement device 104. In some embodiments, each of the machines is identically instrumented, and each machine may include the same number of strain measurement devices. In some instances, the strain measurement device is a wireless fatigue node. It should be noted that while "wireless fatigue nodes" are used herein as an example, any instrumentation that is mapped to damage accumulation may be used instead.

An average damage rate at a specific location for a specific machine may then be defined using the strain measurement devices. This operation may be repeated, and the data may be sent to, and received by, an off-board, near-on board, or on-board system for processing. Method 300 may further include receiving data regarding the amount of time that a machine is used and may be accumulating damage (e.g., calculated via the data from an on-board operation classification system, as described above). The received data may be used to create a histogram of these damage rates for each location that represents the data from all of the instrumented machines. Damage rate histograms may be created for each of the instrumented locations. Each histogram may include a target (e.g. 95%) confidence interval for the damage rate corresponding to the target (e.g., 90th percentile) severity level.

Method 300 may then proceed to operation 304, where a D-optimal row selection calculation is performed on the damage rate basis matrix. In order to solve for the unknown coefficients corresponding to each event in the composite work cycle, the inverse of a matrix must be computed, which involves the determinant of a matrix appearing in a denominator. As a result, locations to measure severity on the system of interest should be chosen to maximize this determinant (i.e., via D-optimal, or determinant optimization).

In some embodiments, method 300 may also detect events missing from the composite work cycle. If the difference between the compared damage rates (the residual) is large, then that would indicate a missing event in the CWC. The absence of an event to be included in the work cycle may then be detected by using the calculated coefficients described above, along with previously determined test event damage rates. With this data, a reconstituted damage rate column vector may be created that closely aligns with an original target (e.g., $90^{th}$) percentile vector (e.g., that was observed in the field or during testing). The shape of the residual column vector would likely provide a clue about what type of an event that might be. If the residual is small, then that would indicate that the current test events are sufficient to adequately span the space of possible machine damage rate column vectors.

Method 300 may also provide multi-collinearity detection. In some embodiments, method 300 may be capable of diagnosing the presence of multi-collinearity before the wireless nodes are placed on machines, thus reducing the probability of project failure. Furthermore, the number of events might be reduced if it is discovered that multi-collinearity exists. In a D-optimal selection process, it is possible to examine whether the condition of multi-collinearity or redundancy exists. Multi-collinearity, in this application, will exist when the damage state on the machine of interest due to one of the basis events can be approximately expressed as a linear combination of the damage states corresponding to the rest of the basis events. That is, redundant test events in the CWC may also be detected by noting whether a damage rate state associated with a particular test event can be nearly expressed as a linear combination of the other damage rate states associated with the other events. If a damage rate state associated with a particular test event can be expressed as a linear combination of the other damage rate states associated with the other events, then the presence of a redundant event in the work cycle may be indicated. The phenomenon may manifest itself in a multitude of varying magnitudes and signs for those events that are involved in the collinearity. Multi-collinearity may be diagnosed via calculation of a variance inflation factor. The presence of multi-collinearity may suggest that the number of operations can be reduced, which in turn suggests a cost-avoidance opportunity.

Method 300 may then proceed to operation 306, where based on the D-optimal row selection calculation, a finite number of strain measurement device locations on the machine are selected. The D-optimal row selection calculation can be used to select a finite number of strain measurement device locations to maximize the usefulness of strain measurement device placement. In some embodiments, an entire damage rate field over some admissible surface of the machine may be used as a candidate set for a D-optimal row selection determination. Particular severity responses (e.g. locations on structures) may be selected via a D-optimal algorithm so as to minimize the uncertainty in the calculation of the coefficients associated with each event. Accordingly, D-optimal criterion is employed in the present embodiment with respect to optimal node placement. Once one or more strain measurement device locations become known, the locations may be selected to receive a strain measurement device in a later test for further model validation. One or more strain measurement device locations may also be selected so as to minimize the variance of the inferred loads. Specifically, strain measurement devices may then be installed at such specified locations on the machine so as to optimize strain measurement device utility. In preferred embodiments, the strain measurement devices 104 may be placed in identical or substantially identical locations on the machine 102. A similar technique may be employed to determine optimal placement of wireless nodes so as to minimize the variance of the unknown (or inferred) coefficients. A change of wireless node location may precipitate a change of strain measurement device location in the basis set. This determination may be accomplished by simulating events with a validated virtual model of machine severity. Thus, the finite number of strain measurement device locations optimizes use of one or more strain measurement devices to be placed on the machine. Method 300 may then proceed to operation 308, where a target percentile damage rate for each of the one or more strain measurement devices is extracted. The method described above and similar methods using statistical inference of work cycle coefficients using D-optimal selection of node locations may be applicable to a variety of machines and systems. In some embodiments, target percentile damage rates may be indirectly calculated. Rows may correspond to different severity responses of a sub-system which has been mapped to a damage rate. Columns may still correspond to events in the work cycle for the sub-system.

Method 300 may then proceed to operation 310, where the extracted damage rates are used to solve for the unknown coefficients in the damage rate basis matrix and verify the weightings assigned to the machine operations. As described above, a least-squares best fit solution for the unknown "{p}" column vector is given by $$\{\hat{p}\}=[[\overline{d}_{bas}]^T[\overline{d}_{bas}]]^{-1}[\overline{d}_{bas}]^T\{\overline{D}_{obs}\}$$

In some embodiments, the unknowns ("{p}") may be solved for via a least-squares pseudo-inverse calculation. In this manner, method 300 provides the ability to determine relative ratios of the events in the composite work cycle, and provide an overall severity multiplier that enables the optimal matching with observed target percentile field damage rates.

Method 300 also provides a determination of optimum strain measurement device locations and a determination of the number of strain measurement devices corresponding to the point of diminishing returns, thereby potentially reducing the amount of hardware needed for a machine. Additionally, the method may be utilized with both standard (i.e. events that the machine typically performs) and contrived (i.e. events that the machine is typically not subjected to, but could be used as endurance testing events) events as inputs.

Simulation may be used to align composite work cycles to targeted percentiles of machine severity distributions, (regardless of which of the two methods above are employed). Simulation may assist with determining which channels should be measured in order to either classify operations or quantify severity. It would be extremely useful in creating empirical relationships between measured quantities and damage rate responses. The parameters of these empirical relationships, as well as their basic form, could also depend upon the current operation of the subsystem.

As an example of the role of simulation, consider the selection of strain measurement device locations for large structure CWC coefficient inference. The process might begin by running OMLA loads through the finite element models of a structural system, resulting in strain time histories and damage rates for all admissible node locations. Submission of this large matrix to a D-optimal row selection routine would result in a reduced-row matrix that may be used as a basis matrix. A random sample of machines may then be instrumented with the wireless nodes at locations corresponding to the D-optimally selected rows.

Data segmentation, as described herein, may also be used in conjunction with method 300, particularly to define operation times for a machine (i.e., the durations during which a machine was being used for a specific purpose and accumulating damage). Data segmentation information may also be used to define composite work cycles for machines introduced into the worksite and writing associated test procedures for those machines. Data segmentation information (received from on-board telematics) may also be utilized to identify severity events missing from the composite work cycle.

It should be appreciated that any of the above described components may embody a single microprocessor or multiple microprocessors known in art. Numerous commercially available microprocessors may be configured to perform the functions of the methods described herein. It should also be appreciated that on and off-board analysis modules used to perform the described methods or systems may readily embody a general microprocessor. A person of ordinary skill in the art will appreciate that on and off-board analysis modules or systems may additionally include other components and may also perform other functionality not described herein. It should be understood that the embodiments, configurations and connections explained herein are merely on an exemplary basis and may not limit the scope and spirit of the disclosure.

INDUSTRIAL APPLICABILITY

The present disclosure provides methods and systems consistent with embodiments of the present disclosure, which allow for CWC events to be defined in such a way so as to create a minimum set of events that adequately span the space of possible received severity responses, and that map to the targeted percentile of reported severity. Therefore, costs will be reduced for product development for both test and simulation-related activities.

Also, the D-optimal approach provides the ability to determine relative ratios of the events in the composite work cycle, and provides an overall severity multiplier that enables the optimal matching with observed target percentile field damage rates. The method also provides a determination of optimum wireless node locations and a determination of the number of wireless nodes corresponding to the point of diminishing returns, thereby potentially reducing the amount of hardware needed for a machine. The method also diagnoses the presence of multi-collinearity before the wireless nodes are placed on machines, thus reducing the probability of project failure. Furthermore, the number of events might be reduced if it is discovered that multi-collinearity exists. The method provides detection of missing events in the composite work cycle can be detected. Additionally, the method may be utilized with both standard and contrived events as inputs.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A method for performing a work operation with a machine based on a composite work cycle damage rate estimate, the method comprising:

constructing, by one or more processors of a computer system, a damage rate basis matrix, wherein:
each row of the damage rate basis matrix corresponds to a location on a machine; and
each column of the damage rate basis matrix corresponds to a test event in a composite work cycle;

performing, by the one or more processors of the computer system, a D-optimal row selection calculation on the damage rate basis matrix to maximize a determinant of the damage rate basis matrix;

assigning the work cycle damage rate estimate to an operation of the machine;

selecting, based on the D-optimal row selection calculation, a finite number of strain measurement device locations on the machine;

placing, on the machine, a strain measurement device at each of the selected strain measurement device locations;

calculating, by the one or more processors of the computer system, a vector of coefficients that, when multiplied by the damage rate basis matrix, results in the extracted target percentile damage rates for each of the one or more strain measurement devices;

verifying, based on a calculated vector of coefficients, weightings assigned to operations of the machine;

transferring, via the one or more processors, the composite work cycle damage rate estimate assigned to an operation of the machine, to one or more on-board modules of the machine; and performing the operation with the machine, using the one or more on-board modules, based on the composite work cycle damage rate estimate.

2. The method of claim 1, wherein:
calculating the vector of coefficients includes performing a pseudo-inverse calculation; and
the vector of coefficients corresponds corresponding to a simulated event.

3. The method of claim 1, wherein:
selecting the finite number of strain measurement device locations on the machine includes selecting optimum strain measurement device locations to calculate the unknown coefficients for a damage test event.

4. The method of claim 3, further comprising:
identifying a number of strain measurement devices corresponding to a point of diminishing returns.

5. The method of claim 4, further comprising:
diagnosing multi-collinearity prior to designating strain measurement device placement locations on a machine.

6. The method of claim 1, further comprising:
detecting one or more redundant test events in a composite work cycle.

7. The method of claim 6, wherein detecting the one or more redundant test events in the composite work cycle includes:
determining if a damage rate calculation is a linear combination of two or more other damage rate calculations in the composite work cycle.

8. The method of claim 1, wherein calculating the vector of coefficients comprises performing a least-squares pseudo-inverse calculation.

9. The method of claim 1, wherein the target percentile damage rates for each of the one or more strain measurement devices are represented as a damage rate column vector, the method further comprising:
analyzing at least one of a delta between at least two test events or a residual vector created from collected test events;
based on the analyzing, determining that one or more test events are missing from the composite work cycle; and
based on the determining, creating a reconstituted damage rate column vector.

10. The method of claim 1, further comprising:
using at least one standard and at least one contrived event as inputs in the D-optimal row selection calculation.

11. One or more non-tangible computer-readable media comprising computer-executable instructions that, when executed on a processor, cause a computing system to perform operations for performing a work operation with a machine based on a composite work cycle damage rate estimate, the operations comprising:
constructing a damage rate basis matrix, wherein:
each row of the damage rate basis matrix corresponds to a location on a machine; and
each column of the damage rate basis matrix corresponds to a test event in a composite work cycle;
performing a D-optimal row selection calculation on the damage rate basis matrix to maximize a determinant of the damage rate basis matrix;
assigning the work cycle damage rate estimate to an operation of the machine;
selecting, based on the D-optimal row selection calculation, a finite number of strain measurement device locations on the machine;
extracting a target percentile damage rate for each of the one or more strain measurement devices;
calculating a vector of coefficients that, when multiplied by the damage rate basis matrix, results in the extracted target percentile damage rates for each of the one or more strain measurement devices;
verifying, based on the calculated vector of coefficients, weightings assigned to operations of the machine operations;
transferring, via one or more processors, the composite work cycle damage rate estimate assigned to the operation of the machine, to one or more on-board modules of the machine; and
performing the operation with the machine, using the one or more on-board modules, based on the composite work cycle damage rate estimate.

12. The one or more non-tangible computer-readable media of claim 11, wherein:
calculating the vector of coefficient includes performing a pseudo-inverse calculation; and
the vector of coefficients corresponds to a simulated event.

13. The one or more non-tangible computer-readable media of claim 11, wherein:
selecting the finite number of strain measurement device locations on the machine includes selecting optimum strain measurement device locations to calculate the unknown coefficients for a damage test event.

14. The one or more non-tangible computer-readable media of claim 13, wherein selecting the finite number of strain measurement device locations on the machine further includes:
identifying a number of strain measurement devices corresponding to a point of diminishing returns.

15. The one or more non-tangible computer-readable media of claim 14, the operations further comprising:
diagnosing multi-collinearity prior to designating strain measurement device placement locations on a machine.

16. The one or more non-tangible computer-readable media of claim 11, the operations further comprising:
detecting one or more redundant test events in a composite work cycle.

17. The one or more non-tangible computer-readable media of claim 16, wherein detecting the one or more redundant test events in the composite work cycle includes:
determining if a damage rate calculation is a linear combination of two or more other damage rate calculations in the composite work cycle.

18. The one or more non-tangible computer-readable media of claim 11, wherein calculating the vector of coefficients comprises performing a least-squares pseudo-inverse calculation.

19. The one or more non-tangible computer-readable media of claim 11, wherein the target percentile damage rates for each of the one or more strain measurement devices are represented as a damage rate column vector, the operations further comprising:
analyzing at least one of a delta between at least two test events or a residual vector created from collected test events;
based on the analyzing, determining that one or more test events are missing from the composite work cycle; and
based on the determining, creating a reconstituted damage rate column vector.

20. A system for performing a work operation with a machine based on a composite work cycle damage rate estimate, the system comprising:
an analysis module configured to:
construct a damage rate basis matrix, wherein:
each row of the damage rate basis matrix corresponds to a location on the machine; and
each column of the damage rate basis matrix corresponds to a test event in a composite work cycle;
perform a D-optimal row selection calculation on the damage rate basis matrix to maximize a determinant of the damage rate basis matrix;

select, based on the D-optimal row selection calculation, a finite number of strain measurement device locations on the machine;

calculate a vector of coefficients that, when multiplied by the damage rate basis matrix, results in the extracted target percentile damage rates for each of the one or more strain measurement devices;

transfer, via one or more processors, the composite work cycle damage rate estimate assigned to an operation of the machine, to one or more on-board modules of the machine; and perform the operation with the machine, using the one or more on-board modules, based on the composite work cycle damage rate estimates.

* * * * *